US008501917B2

(12) United States Patent
Kim et al.

(10) Patent No.: US 8,501,917 B2
(45) Date of Patent: Aug. 6, 2013

(54) ANTI C-MET ANTIBODY AND USES THEREOF

(71) Applicant: Samsung Electronics Co., Ltd., Suwon-si (KR)

(72) Inventors: Bo-gyou Kim, Seoul (KR); Yun-ju Jeong, Anyang-si (KR); Kyung-ah Kim, Seongnam-si (KR); Kwang-ho Cheong, Seoul (KR); Seung-hyun Lee, Suwon-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 13/679,852

(22) Filed: Nov. 16, 2012

(65) Prior Publication Data
US 2013/0129731 A1 May 23, 2013

(30) Foreign Application Priority Data

Nov. 17, 2011 (KR) ........................ 10-2011-0120317

(51) Int. Cl.
*C07K 16/26* (2006.01)
*C07K 16/00* (2006.01)
*A61K 39/395* (2006.01)
*C07H 21/04* (2006.01)
*C12N 1/20* (2006.01)
*C12N 5/20* (2006.01)

(52) U.S. Cl.
USPC ............. 530/388.24; 530/388.1; 530/387.1; 424/145; 424/141.1; 424/130.1; 536/23.53; 435/252.3; 435/328; 435/326

(58) Field of Classification Search
None
See application file for complete search history.

(56) References Cited

U.S. PATENT DOCUMENTS 7,498,420 B2 * 3/2009 Michaud et al. ......... 530/388.15

FOREIGN PATENT DOCUMENTS

| WO | WO 2009/051344 A2 | 4/2009 |
| WO | WO 2009/079585 A2 | 6/2009 |
| WO | WO 2011/050242 A1 | 4/2011 |

OTHER PUBLICATIONS

Song et al., "Successful Application of the Dual-Vector System II in Creating a Reliable Phage-Displayed Combinatorial Fab Library," *Mol. Cells*, 27: 313-319 (2009).

* cited by examiner

*Primary Examiner* — Sharon Wen
(74) *Attorney, Agent, or Firm* — Leydig, Voit & Mayer, Ltd.

(57) ABSTRACT

An anti c-Met antibody or antigen-binding fragment thereof comprising a heavy-chain variable region having heavy-chain complementarity determining region (CDR) amino acid sequences of SEQ ID NOs: 1, 2 and 3, and a light-chain variable region having light-chain CDR amino acid sequences of SEQ ID NOs: 4, 5, and 6; and a method of wound healing, tissue regeneration, or cell proliferation comprising administration of same; as well as related compositions and methods.

22 Claims, 6 Drawing Sheets

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR1 sequence of heavy chain of IGTML4-4
      antibody

<400> SEQUENCE: 1

Met Tyr Val Met Thr
1               5
```

```
<210> SEQ ID NO 2
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR2 sequence of heavy chain of IGTML4-4
      antibody

<400> SEQUENCE: 2

Glu Ile Ser Ala Ser Gly Ala Ser Thr Tyr Tyr Ala Asp Ser Val Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR3 sequence of heavy chain of IGTML4-4
      antibody

<400> SEQUENCE: 3

Ala Tyr Arg Tyr Gly Met Asp Val
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR1 sequence of light chain of IGTML4-4
      antibody

<400> SEQUENCE: 4

Arg Ala Ser Gln Asn Ile Gly Ser Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: CDR2 sequence of light chain of IGTML4-4
      antibody

<400> SEQUENCE: 5

Arg Ala Ser Asn Leu Arg Ser
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<223> OTHER INFORMATION: CDR3 sequence of light chain of IGTML4-4
      antibody

<400> SEQUENCE: 6

Gln Gln Ala Thr Ile Phe Pro
1               5

<210> SEQ ID NO 7
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of heavy chain variable
      region of IGTML4-4 antibody

<400> SEQUENCE: 7

Gln Val Gln Leu Leu Gln Ser Gly Gly Gly Leu Val Gln Pro Gly Gly
1               5                   10                  15

Ser Leu Arg Val Ser Cys Ala Ala Ser Gly Phe Arg Phe Ser Met Tyr
            20                  25                  30

Val Met Thr Trp Val Arg Gln Ala Pro Gly Lys Gly Leu Glu Trp Val
        35                  40                  45

Ser Glu Ile Ser Ala Ser Gly Ala Ser Thr Tyr Tyr Ala Asp Ser Val
    50                  55                  60

Lys Gly Arg Phe Thr Met Ser Arg Asp Asn Ser Lys Asn Thr Val Phe
65                  70                  75                  80

Leu Gln Met Asn Ser Leu Arg Val Glu Asp Thr Ala Val Tyr Tyr Cys
                85                  90                  95

Ala Arg Ala Tyr Arg Tyr Gly Met Asp Val Trp Gly Gln Gly Thr Met
            100                 105                 110

Val Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of light chain variable
      region of IGTML4-4 antibody

<400> SEQUENCE: 8

Asp Ile Val Met Thr Gln Ser Pro Ser Ser Val Ser Ala Ser Val Gly
1               5                   10                  15

Asp Arg Val Thr Leu Thr Cys Arg Ala Ser Gln Asn Ile Gly Ser Trp
            20                  25                  30

Leu Ala Trp Tyr Gln Gln Lys Pro Gly Asn Ala Pro Lys Leu Leu Ile
        35                  40                  45

Tyr Arg Ala Ser Asn Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Thr Ile Phe Pro Leu
                85                  90                  95

Thr Phe Gly Gly Gly Thr Arg Val Asp Ile Lys Arg
            100                 105
```

<210> SEQ ID NO 9
<211> LENGTH: 351
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of heavy chain variable
      region of IGTML4-4 antibody

<400> SEQUENCE: 9
caggtgcagc tgttgcagtc tggggaggc ttggtacagc ctgggggtc cctaagagtc      60 tcctgtgcag cctctggatt caggtttagt atgtatgtca tgacgtgggt ccgccaggct     120
ccagggaagg ggctggagtg ggtctcagaa ataagtgcta gcggtgcgag cacatactac     180
gcagactccg tgaagggccg gttcaccatg tccagagaca attccaagaa tacggtgttt     240
ctgcaaatga acagcctgag agtcgaggac acggccgtct attactgtgc aagagcctat     300
aggtacggta tggacgtctg gggccaagga accatggtca ccgtctcctc a             351

<210> SEQ ID NO 10
<211> LENGTH: 324
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: nucleotide sequence of light chain variable
      region of IGTML4-4 antibody

<400> SEQUENCE: 10
gatattgtga tgacccagtc tccatcttcc gtgtctgcat ctgttggaga cagagtcacc      60
ctcacttgtc gggcgagtca gaatattggc agctggttag cctggtatca gcagaaacca     120
ggtaacgccc ctaagttgtt gatctataga gcatccaatt tgcgaagtgg ggtcccatca     180
aggttcagcg gcagtggctc tgggacagat ttcactctta ccatcagcag cctgcagcct     240
gaagatttcg caacttactt ttgtcaacag gctaccattt ccctctcac tttcggcgga     300 gggacccggg tggatatcaa acgt                                            324

<210> SEQ ID NO 11
<211> LENGTH: 97
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of heavy chain constant
      region of IGTML4-4 antibody

<400> SEQUENCE: 11

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr

```
65                  70                  75                  80
Ile Cys Asn Val Asn His Lys Pro Ser Asn Thr Lys Val Asp Lys Lys
                    85                  90                  95

Val

<210> SEQ ID NO 12
<211> LENGTH: 106
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: amino acid sequence of light chain constant
      region of IGTML4-4 antibody

<400> SEQUENCE: 12

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105
```

ANTI C-MET ANTIBODY AND USES THEREOF

CROSS-REFERENCE TO RELATED APPLICATIONS

This application claims the benefit of Korean Patent Application No. 10-2011-0120317, filed on Nov. 17, 2011, and all the benefits accruing therefrom under 35 U.S.C. §119, the disclosure of which is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 7,830 Byte ASCII (Text) file named "711030_ST25.txt," created on Nov. 16, 2012.

BACKGROUND

1. Field

The present disclosure relates to an anti c-Met antibody, or an antigen-binding fragment thereof, a pharmaceutical composition for wound healing or tissue regeneration that includes the anti c-Met antibody or antigen-binding fragment thereof, and a composition for facilitating cell proliferation.

2. Description of the Related Art c-Met is a typical receptor tyrosine kinase (RTK) present on a cell surface that induces intracellular signal transmission by binding with its ligand hepatocyte growth factor (HGF), thereby facilitating cell growth. Studies conducted so far have revealed that c-Met is found in various human tissues of damaged organs, including the liver, lung, kidney, heart, intestinal mucosa, and skin, and thus is involved in post-damage regeneration of such tissues. c-Met may facilitate liver tissue regeneration after a hepatectomy or damage from liver cancer or cirrhosis; kidney tissue regeneration after simple or partial kidney resection from cancer, infection, renal stones, or renal artery stricture; skin tissue regeneration in patients with skin damage from burns, bedsores, or skin ulcers; and heart tissue regeneration after damage from cardiac infarction.

c-Met is involved in a variety of mechanisms, for example, cancer occurrence, metastasis, cancer cell migration and invasion and angiogenesis, and in the growth of a variety of cells. Further to the ability to facilitate regeneration and growth of normal tissue cells such as liver, kidney and heart cells, c-Met is known to facilitate growth and proliferation of stem cells when bound to a growth factor HGF.

SUMMARY

Provided is an anti c-Met antibody or an antigen-binding fragment thereof. In one aspect, the antibody or antibody fragment comprises a heavy-chain variable region having heavy-chain complementarity determining region (CDR) amino acid sequences of SEQ ID NOs. 1, 2 and 3, and a light-chain variable region having light-chain CDR amino acid sequences of SEQ ID NOs. 4, 5, and 6. In another aspect, the antibody or antibody fragment comprises a heavy-chain variable region having an amino acid sequence of SEQ ID No. 7, and a light-chain variable region having an amino acid sequence of SEQ ID No. 8. Polynucleotides encoding the antibody or antibody fragment, and related compositions also are provided.

Further provided are methods for wound healing, tissue regeneration, and cell proliferation that include administration to a subject the anti c-Met antibody or antigen-binding fragment thereof.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
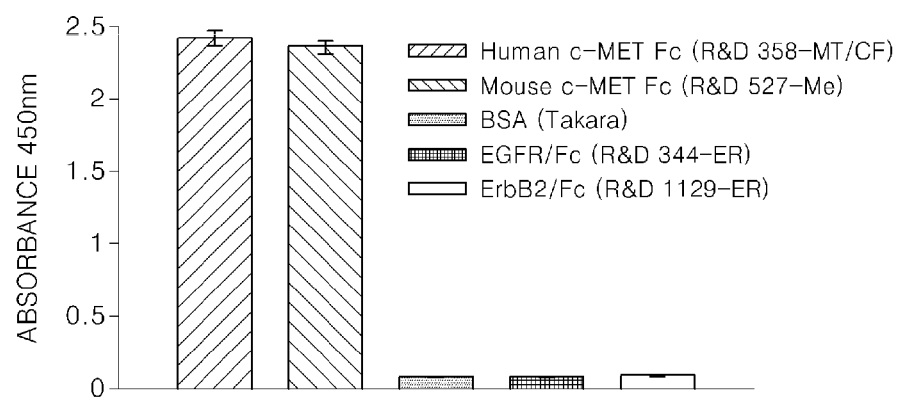
FIG. 1 is a graph presenting results of an enzyme-linked immunosorbent assay (ELISA), indicating recognition of an anti c-Met antibody in different species, according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be constructed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an embodiment of the present disclosure, an anti c-Met antibody or antigen-binding fragment thereof includes a heavy-chain variable region having heavy-chain complementarity determining region (CDR) amino acid sequences of SEQ ID NOs: 1, 2 and 3, and a light-chain variable region having light-chain CDR amino acid sequences of SEQ ID NOs: 4, 5, and 6.

In some embodiments, the anti c-Met antibody or antigen-binding fragment thereof may include a heavy-chain variable region having an amino acid sequence of SEQ ID NO: 7, and a light-chain variable region having an amino acid sequence of SEQ ID NO: 8. In some embodiments, the anti c-Met antibody or antigen-binding fragment thereof may include a heavy-chain constant region having an amino acid sequence of SEQ ID NO. 11, and/or a light-chain variable region having an amino acid sequence of SEQ ID NO. 12.

The terms "c-Met" or "c-Met protein" means a receptor tyrosine kinase (RTK) that binds to a hepatocyte growth factor (HGF). The c-Met protein may include, for example, polypeptides encoded by nucleotide sequences of GenBank Accession Number NM_000245, proteins encoded by polypeptide sequences of GenBank Accession Number NM_000236, or extracellular domains thereof. The RTK c-Met is involved in a variety of mechanisms, for example, cancer occurrence, metastasis, cancer cell migration and invasion, angiogenesis, cell migration, and cell proliferation.

In an embodiment of the present disclosure, the antibody may be a monoclonal antibody.

An intact antibody or immunoglobulin includes four polypeptides: two full-length light chains and two full-length heavy chains, in which each light chain is linked to a heavy chain by disulfide bonds. An antibody may include a heavy-chain constant region and a light-chain constant region, wherein the heavy-chain constant region may be of type γ (gamma), μ (mu), α (alpha), δ (delta), or ε (epsilon), and may have subclasses of γ1, γ2, γ3, γ4, α1, and α2. The light-chain constant region can be either a kappa (K) or lambda (Λ) type.

The term "heavy chain" is taken to include a full-length heavy chain and fragments thereof, the full-length heavy chain including a variable region $V_H$ having amino acid sequences that determine specificity for antigens, a constant region having three constant domains $C_{H1}$, $C_{H2}$, and $C_{H3}$, and a hinge region. The term "light chain" is taken to include a full-length light chain and fragments thereof, the full-length light chain including a variable region $V_L$ having amino acid sequences that determine specificity for antigens, and a constant region $C_L$.

The term "complementarity determining region (CDR)" means an amino acid sequence found in the variable region of a heavy chain or a light chain of an immunoglobulin. The heavy and light chains may each include three CDRs (CDRH1, CDRH2, and CDRH3; and CDRL1, CDRL2, and CDRL3). The CDRs determine the specificity of an antibody and may provide a contact residue for binding to a specific epitope of an antigen. The terms "specifically binding" or "specifically detected" has the same meaning as a generically used term in the art, and means an immunological reaction between an antibody and antigen via a specific interaction.

According to another embodiment of the present disclosure, an antigen-binding fragment of the anti c-Met antibody includes a heavy-chain variable region having heavy-chain CDR amino acid sequences of SEQ ID NOs: 1, 2 and 3, and a light-chain variable region having light-chain CDR amino acid sequences of SEQ ID NOs: 4, 5, and 6.

In some embodiments, the antigen-binding fragment may be selected from the group consisting of scFv, (scFv)$_2$, Fab, Fab', and F(ab')$_2$, but is not limited thereto.

The term "antigen-binding fragment" used herein refers to fragments of an intact immunoglobulin, and any part of a polypeptide including antigen binding regions having the ability to specifically bind to the antigen. The antigen-binding fragment Fab, which includes the light-chain and heavy-chain variable regions, the light-chain constant region, and the heavy-chain constant region $C_{H1}$, has one antigen-binding site. The antigen-binding fragment Fab' differs from Fab, in that Fab' includes a hinge region with at least one cysteine residue at a C-terminal of the heavy-chain constant domain $C_{H1}$. The F(ab')$_2$ antibody is generated through disulfide bridging of the cysteine residue of the Fab' hinge region. Fv is a least antibody fragment with only variable regions of heavy chain and light chain. Recombination technologies of generating the Fv fragment are widely known in the art. Two-chain Fv includes heavy-chain and light-chain variable regions linked by non-covalent bonds. Single-chain Fv includes, in general, heavy-chain and light-chain variable regions linked by covalent bonding via a peptide linker, or may form a dimer structure, like the two-chain Fv, with heavy-chain and short-chain variable regions directly linked at C-terminals. These antigen-binding fragments may be attainable using protease (for example, the Fab fragment may be obtained by restriction-cleavage of a whole antibody with papain, and the F(ab')$_2$ fragment may be obtained by cleavage with pepsin), or may be constructed using gene recombination technologies.

In some embodiments the c-Met may originate from a mammal, such as a human, a monkey, a mouse, and a rat.

In some embodiments, since having a strong binding force both to human c-Met and mouse c-Met, the anti c-Met antigen or antigen-binding fragment thereof may be advantageous for use in animal tests for the development of a pharmaceutical composition containing the same.

According to another embodiment of the present disclosure, there is provided a polynucleotide encoding an anti c-Met antibody or an antigen-binding fragment thereof, the anti c-Met antibody including a heavy-chain variable region having heavy-chain CDR amino acid sequences of SEQ ID NOs. 1, 2 and 3, and a light-chain variable region having light-chain CDR amino acid sequences of SEQ ID NOs. 4, 5, and 6.

According to another embodiment of the present disclosure, there is provided a polynucleotide encoding an anti c-Met antibody or an antigen-binding fragment thereof that includes a heavy-chain variable region having an amino acid sequence of SEQ ID NO: 7 and a light-chain variable region having an amino acid sequence of SEQ ID NO: 8. In some embodiments, the anti c-Met antibody or antigen-binding fragment thereof may include a heavy-chain constant region having an amino acid sequence of SEQ ID NO. 11, and a light-chain variable region having an amino acid sequence of SEQ ID NO. 12.

In some embodiments, the polynucleotide encoding the heavy-chain region having the amino acid sequence of SEQ ID NO: 7 may include a nucleotide sequence of SEQ ID NO: 9. The polynucleotide for encoding the heavy-chain variable region having the amino acid sequence of SEQ ID NO: 8 may include a nucleotide sequence of SEQ ID NO: 10.

As used herein, the term "polynucleotide" means a polymer of single-stranded or double-stranded deoxyribonucleic acid or ribonucleic acid. The polynucleotide includes RNA genome sequences, DNA (gDNA and cDNA), and RNA sequences transcribed therefrom, and additionally includes analogues of natural polynucleotides, unless specifically mentioned otherwise.

The polynucleotide also includes nucleotide sequences encoding the amino acid sequences of the heavy or light chain variable regions of the antibody specifically binding to c-Met protein and nucleotide sequences complementary thereto. The complementary sequences include completely complementary sequences and substantially complementary sequences. For example, substantially complementary sequences are sequences that may be hybridized with the nucleotide sequences encoding the amino acid sequences of the heavy or light chain variable regions of the anti c-Met antibody under stringent conditions known in the art.

The nucleotide sequences encoding the amino acid sequences of the heavy and light chain variable regions may be mutated. The mutations include addition, deletion, and/or substitution. A polynucleotide encoding the amino acid sequence of a heavy or light chain variable region of an antibody specifically binding to c-Met protein is understood to include nucleotide sequences substantially identical to the nucleotide sequences described above. Substantially identical nucleic acid sequences may be sequences with at least 80% sequence identity, at least 90% sequence identity, or at least 95% sequence identity to the above described nucleotide sequences, when the sequences are aligned to correspond to each other as much as possible, wherein the aligned nucleotide sequences are analyzed using any algorithm used in the art.

According to an embodiment of the present disclosure, there is provided a recombinant vector including a polynucleotide encoding an anti c-Met antibody or an antigen-binding fragment thereof, the anti c-Met antibody including a heavy-chain variable region having heavy-chain CDR amino acid sequences of SEQ ID NOs: 1, 2, and 3, and a light-chain variable region having light-chain CDR amino acid sequences of SEQ ID NOs: 4, 5, and 6.

In some embodiments, the recombinant vector includes a polynucleotide encoding an anti c-Met antibody or an antigen-binding fragment thereof including a heavy-chain variable region having an amino acid sequence of SEQ ID NO. 7 and a light-chain variable region having an amino acid sequence of SEQ ID NO. 8. In some embodiments, the anti c-Met antibody or antigen-binding fragment thereof may include a heavy-chain constant region having an amino acid sequence of SEQ ID NO. 11, and a light-chain variable region having an amino acid sequence of SEQ ID NO. 12.

The term "vector" used herein refers to a polynucleotide for expressing a target gene in a host cell. For example, the vector may include a plasmid vector, a cosmid vector, and a virus vector, such as a bacteriophage vector, an adenovirus vector, a retrovirus vector, and an adeno-associated virus vector. Suitable recombinant vectors may be constructed by manipulating plasmids known in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (for example, λgt4λB, λ-Charon, λΔz1, and M13), or a virus (for example, SV40).

In the recombinant vector, the polynucleotides encoding the amino acid sequences of the heavy and light chain variable regions may be operatively linked to a promoter. The term "operatively linked" used herein refers to a functional linkage between a nucleotide expression regulating sequence (for example, a promoter sequence) and other nucleotide sequences. Thus, the nucleotide expression regulating sequence may regulate the transcription and/or translation of the other nucleotide sequences.

The recombinant vector may be constructed for cloning or expression. The expression vector may be any vector known in the art for expressing an exogenous protein in plants, animals, or microorganisms. The recombinant vector may be constructed using various methods known in the art.

The recombinant vector may be constructed using a prokaryotic cell or a eukaryotic cell as a host. For example, when a prokaryotic cell is used as a host cell, the expression vector used generally includes a strong promoter capable of initiating transcription (for example, $p_L^\lambda$ promoter, trp promoter, lac promoter, tac promoter, T7 promoter), a ribosome binding site for initiating translation, and a transcription/translation termination sequence. When a eukaryotic cell is used as a host cell, the vector used generally includes the origin of replication acting in the eukaryotic cell, for example, a f1 replication origin, a SV40 replication origin, a pMB1 replication origin, an adeno replication origin, an AAV replication origin, or a BBV replication origin, but is not limited thereto. A promoter in an expression vector for a eukaryotic host cell may be a promoter derived from the genomes of mammalian cells (for example, a metallothionein promoter) or a promoter derived from mammalian viruses (for example, an adenovirus late promoter, a vaccinia virus 7.5K promoter, a SV40 promoter, a cytomegalovirus promoter, and a tk promoter of HSV). A transcription termination sequence in an expression vector for a eukaryotic host cell may be, in general, a polyadenylation sequence.

A vector system capable of expressing the heavy and light chain variable regions of the antibody may be a vector system in which the heavy and light chain variable regions are simultaneously expressed from a single vector, or a system in which the heavy and light chain variable regions are each independently expressed from separate vectors. In the latter case, the two vectors may be introduced into the host cell by co-transformation and targeted transformation.

According to an embodiment of the present disclosure, there is provided a host cell including a polynucleotide encoding an anti c-Met antibody or an antigen-binding fragment thereof, the anti c-Met antibody including a heavy-chain variable region having heavy-chain CDR amino acid sequences of SEQ ID NOs: 1, 2, and 3, and a light-chain variable region having light-chain CDR amino acid sequences of SEQ ID NOs: 4, 5, and 6.

In some other embodiments, the host cell may include a polynucleotide encoding an anti c-Met antibody or an antigen-binding fragment thereof including a heavy-chain variable region having an amino acid sequence of SEQ ID NO. 7 and a light-chain variable region having an amino acid sequence of SEQ ID NO. 8. In some embodiments, the anti c-Met antibody or antigen-binding fragment thereof may include a heavy-chain constant region having an amino acid sequence of SEQ ID NO. 11, and a light-chain variable region having an amino acid sequence of SEQ ID NO. 12.

Any host cell known in the art to enable stable and continuous cloning or expression of the recombinant vector may be used. Suitable prokaryotic host cells may include *E. coli* JM109, *E. coli* BL21, *E. coli* RR1, *E. coli* LE392, *E. coli* B, *E. coli* X 1776, *E. coli* W3110, *Bacillus* species strains such as *Bacillus subtillis* or *Bacillus thuringiensis*, intestinal bacteria and strains such as *Salmonella typhymurum, Serratia marcescens*, and various *Pseudomonas* species. Suitable eukaryotic host cells to be transformed may include yeasts, such as *Saccharomyce cerevisiae*, insect cells, plant cells, and animal cells, for example, Sp2/0, Chinese hamster ovary (CHO) K1, CHO DG44, PER.C6, W138, BHK, COS-7, 293, HepG2, Huh7, 3T3, RIN, and MDCK cell lines.

The recombinant vector including the polynucleotide may be transferred into a host cell by using known transfer methods. Suitable transfer methods may be chosen according to the host cell. Suitable transfer methods for prokaryotic host cells may include a method using $CaCl_2$ and electroporation. Suitable transfer methods for eukaryotic host cells may include microinjection, calcium phosphate precipitation, electroporation, liposome-mediated transfection, and gene bombardment. However, any suitable transfer method may be used.

When a microorganism, such as *E. coli*, is used as the host cell, the production of antibodies is higher than that in an animal cell. However, a microorganism is not suitable for producing intact Ig-type antibodies due to lack of glycosylation of the antibodies produced, although a microorganism may be used for producing antigen-binding fragments of an antibody such as Fab and Fv.

A transformed host cell may be selected using a phenotype expressed by a selected marker by any method known in the art. For example, if the selected marker is a gene that is resistant to a specific antibiotic, a transformant is cultured in a medium including the antibiotic, and thus the transformant may be easily selected.

According to an embodiment of the present disclosure, there is provided a pharmaceutical composition comprising the anti-c-Met antibody or antigen-binding fragment thereof, as described herein, and a pharmaceutically acceptable carrier, a diluent, or an excipient. The pharmaceutical composition can be used for any purpose, including, for instance, wound healing or tissue regeneration, or facilitating cell proliferation.

Thus, also provided herein is a method for would healing or tissue regeneration that comprises administering (e.g., to a subject) the anti c-Met antibody or an antigen-binding fragment, optionally in a pharmaceutical composition.

In some embodiments, non-limiting examples of tissues that may be regenerated with the pharmaceutical composition are liver tissues, lung tissues, kidney tissues, heart tissues, intestinal mucosa tissues, and skin tissues.

The pharmaceutical composition may include a pharmaceutical acceptable carrier. Non-limiting examples of the pharmaceutically acceptable carrier that may be used in the pharmaceutical are commonly used lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil. The pharmaceutical composition may further include, for example, a lubricant, a wetting agent, a sweetener, a flavor enhancer, an emulsifying agent, a dispersing agent, and/or a preservative.

The pharmaceutical composition may be administered orally or parenterally. Examples of the parenteral administration are intravenous injection, subcutaneous injection, muscular injection, intraperitoneal injection, endothelial administration, local administration, intranasal administration, intrapulmonary administration, and rectal administration. Since oral administration leads to digestion of a protein or peptide, the pharmaceutical composition to be orally administered preferably is coated with an active ingredient or formulated to be resistant against digestion in the stomach. The pharmaceutical composition may be administered using any device that may help migration of an active component to a target cell.

A suitable dosage of the pharmaceutical composition may depend on a variety of factors, including formulation methods, administration methods, ages of patients, body weight, gender, pathologic conditions, diets, administration time, administration route, excretion speed, and reaction sensitivity. A dosage of the pharmaceutical composition may be from about 0.001 to about 100 mg/kg for an adult. The term "therapeutically effective amount" or "pharmaceutically effective amount" used herein refers to a sufficient amount for wound healing or tissue regeneration, or facilitating cell proliferation.

The pharmaceutical composition may be formulated with a pharmaceutically acceptable carrier and/or an excipient in the form of a unit or multiple dosage(s) by a well-known method in the art. In this regard, the formulation may be a solution in oil or an aqueous medium, a suspension, a syrup, an emulsifying solution, an extract, powder, granules, a tablet, or a capsule, and may further include a dispersing or a stabilizing agent. In addition, the pharmaceutical composition may be administered as an individual drug, or together with other drugs, and may be administered sequentially or simultaneously with existing treatment drugs. The pharmaceutical composition including the c-Met antibody or antigen binding fragment thereof may be formulated as an immunoliposome. The antibody-containing liposome may be prepared using any method known in the art. The immunoliposome, which is a lipid composition including phosphatidylcholine, cholesterol, and polyethyleneglycol-derived phosphatidylethanolamine, may be prepared by reverse phase evaporation. For example, Fab' fragments may be adhered to the liposome through a thiol-disulfide exchange reaction. In some embodiments the antibody may be an antigen-binding fragment selected from the group consisting of scFv, $(scFv)_2$, Fab, Fab', and $F(ab')_2$.

In some embodiments, the antibody may be an agonist of c-Met protein.

The term "agonist" used herein is understood to include any molecule that partially or entirely blocks, inhibits, and/or neutralizes at least one biological activity of a target material (for example, c-Met). For example, the term "agonist antibody" refers to an antibody that induces or increases the biological activity of an antigen (for example, c-Met) to which the antibody binds. An agonist may facilitate a receptor's phosphorylation due to binding of the receptor to a ligand or may activate or grow cells deactivated by the ligand. An agonist may completely activate receptor-ligand interaction or may practically facilitate the receptor-ligand interaction through change in a tertiary structure of the receptor or up regulation of the receptor.

According to another embodiment, a method for facilitating cell proliferation is provided, which comprises administering (e.g., to a subject) the anti c-Met antibody or an antigen-binding fragment thereof, optionally as part of a pharmaceutical formulation.

The anti c-Met antibody or antibody fragment described herein may serve as an agonist of c-Met protein, and thus may facilitate cell proliferation and be used in a composition for cell proliferation. A recent study revealed that c-Met is involved in the generation and maintenance of stem cells (Proceedings of the National Academy of Sciences of the U.S.A. (PNAS), Jun. 14, 2011; 108(24); 9951-6). Accordingly, the anti-c-Met antibody or antibody fragment described herein, or pharmaceutical composition comprising same, may be added to a culture liquid for use in the maintenance and proliferation of stem cells. The pharmaceutical composition may facilitate proliferation of protein-producing (for example, CHO and HEK293) expressing c-Met on a surface thereof, and thus be used to increase yield of the protein expressed on cell lines.

One or more embodiments of the present disclosure will now be described in detail with reference to the following examples. However, these examples are for illustrative purposes only and are not intended to limit the scope of the one or more embodiments of the present disclosure.

Example 1

Screening of Polypeptide Specifically Binding to c-Met and Production of Anti c-Met Antibody Biopanning was performed using bead panning. In particular, magnetic beads (available from Invitrogen) with streptavidin attached to surfaces of the beads and a c-Met antigen (available from R&D systems) with biotin bound thereto were mixed together to obtain a mixture, which was then stirred at about 4° C. for about 18 hours to immobilize the c-Met antigen on the surface of the magnetic beads. The magnetic beads with the c-Met antigen immobilized thereon were blocked with skim milk at room temperature for about 2 hours, and then the c-Met antigen-conjugated beads were put into a solution containing a phage display polypeptide library with a diversity of about $10^{18}$. The resultant mixture was stirred for about 2 hours, and then, only phages bound to the c-Met antigen were selectively separated from the solution. This method was to remove unbound phages through washing with a magnetic bar, but not to separate the antigen-conjugated beads and the antigen-phase bound beads from each other. After the washing, the c-Met antigen and phages were separated from each other with an elution buffer (0.2 M Glycine-HCl, pH 2.2), followed by isolation of the phases from the beads using the magnetic bar.

After amplification of the isolated phage by using transfection E. coli, repeated biopanning was performed. The biopanning process began with screening out of human c-Met-bound polypeptides by using human c-Met-conjugated beads. Afterwards, mouse c-Met-bound antibodies were selected from among the screened-out polypeptides by using mouse c-Met-conjugated beads, followed by screening out of human c-Met-bound polypeptides by using human c-Met-conjugated beads.

Through the above-described biopanning process, polypeptides specifically binding to both the human and mouse c-Met were obtained. The biopanning process also enabled simultaneous antibody optimization and affinity maturation in constructing antibodies. Antibody optimization and affinity maturation are for increasing affinity of heavy chains of selected antibodies through shuffling with a human light-chain library. In particular, a Fab library was constructed using the human light-chain library with the heavy-chains of the selected antibodies immobilized, and then panning was performed with the Fab library, followed by phage amplification and selection of high-affinity antibodies among the selected antibodies.

Through the biopanning process polypeptides specifically binding both the human c-Met and mouse c-Met were obtained. The polypeptide sequences are shown in Table 1 below. Construction of c-Met antibodies from these polypeptides (CDR sequences) was entrusted to IG Therapy Co. (South Korea). The constructed antibodies were named IGTML4-4.

TABLE 1

| | CDR1 | CDR2 | CDR3 |
|---|---|---|---|
| Heavy-chain CDR sequences if IGTML4-4 antibody | MYVMT (SEQ ID NO: 1) | EISASGASTYYADSVKG (SEQ ID NO: 2) | AYRYGMDV (SEQ ID NO: 3) |
| Light-chain CDR sequences of IGTML4-4 antibody | RASQNIGSWLA (SEQ ID NO: 4) | RASNLRS (SEQ ID NO: 5) | QQATIFP (SEQ ID NO: 6) |

Example 2

Determination of Recognition of c-Met from Different Species of IGTML4-4 Antibody The IGTML4-4 antibodies constructed in Example 1 are able to recognize both human and mouse c-Met, which was confirmed using an enzyme-linked immunosorbent assay (ELISA).

50 μL (2 μg/mL) of human or mouse c-Met/Fc fusion protein (available from R&D Systems, Inc.) was added and attached to a well of a plate. Unreacted antigen was removed by washing. EGFR/Fc fusion protein (available from R&D Systems) and ErbB2/Fc fusion protein (available from R&D Systems) were used as control groups. 50 ng of the IGTML4-4 antibody was added to each well and incubated with the antigen for about 1 hour, followed by sufficient washing with a phosphoric acid buffer-Tween 20 (TBS-T20) solution to removed unreacted antibodies. A goat anti-human IgG-horseradish peroxidase (IgG-HRP) was added to the well, incubated at room temperature for about 1 hour, and then was sufficiently washed with TBS-T20 solution. Subsequently, o-phenylenediamine (OPD) solution was added, and the degree of peroxidase reaction was evaluated by an absorbance measurement at 450 nm using an ELISA reader (available from Bio-Rad), to determine whether the IGTML4-4 antibody was bound to both the human and mouse c-Met proteins.

Referring to FIG. 1, the IGTML4-4 antibody was found to be able to recognize both the human c-Met and mouse c-Met, but not a receptor tyrosin kinase (RTK) EGFR or ErbB2.

Example 3

Analysis of IGTML4-4 Antibody's Affinity to Antigen

Binding affinity of the IGTML4-4 antibody constructed in Example 1 to c-Met antigens was analyzed using a Biacore (available from GE Healthcare). After immobilization of about 100-200 RU of each antibody on a CM5 chip, the human c-Met and mouse c-Met antigens were added in 9 different concentrations ranging from about 50 nM to about 0 nM at an injection rate of about 30 μl/min, to obtain $k_{on}$ and $k_{off}$ values, from which $K_D$ values were calculated. The results are shown in Table 2 below. Referring to Table 2, the IGTML4-4 antibodies were found to have a high binding affinity with a $K_D$ value of less than 1 nM, both to the human c-Met and mouse c-Met.

TABLE 2

| Antigen | $k_{on}$ (1/Ms) | $k_{off}$ (1/s) | $K_D$ (nM) |
|---|---|---|---|
| Human c-Met | $4.71 \times 10^5$ | $1.88 \times 10^{-4}$ | 0.398 |
| Mouse c-Met | $5.53 \times 10^5$ | $1.68 \times 10^{-4}$ | 0.304 |

Example 4

Test of c-Met Pathway Activation by IGTML4-4 Antibody in Caki-1 Cells

To compare agonisms of the IGTML4-4 antibody of Example 1, degrees of Akt (protein kinase B) phosphorylation as a critical index involved in down-stream signal transduction of c-Met and cell proliferation were measured using Caki-1 cells (purchased from the Korean Cell Line Bank (KCLB, Seoul, Korea)). Mouse IgG was used as a negative control group, and a 5D5 antibody known as an agonist was used as a positive control group.

Caki-1 cells ($2 \times 10^5$ cells/ml) were portioned into a 96-well plate, and after about 24 hours, each well was added to 5 μg/ml of the IGTML4-4 antibody in serum-free conditions for about 30 minutes. After lysis of the cells incubated with the IGTML4-4 antibody, degrees of Akt phosphorylation were measured and analyzed using a PathScan phospho-AKT1 (Ser473) chemiluminescent Sandwich ELISA kit (Cat. No. 7134S, available from Cell Signaling).

Figure 2:
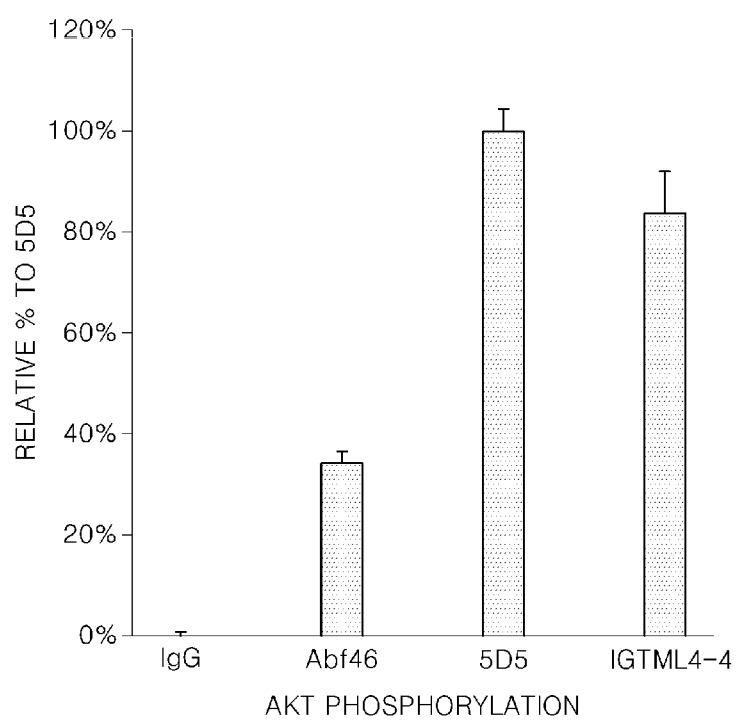
FIG. 2 is a graph presenting degrees of Akt phosphorylation by an anti c-Met antibody according to an embodiment of the present disclosure.

Referring to FIG. 2, the IGTML4-4 antibody was found to have about 84% degree of Akt phosphorylation relative to the 5D5 antibody. This indicates that the IGTML4-4 antibody may function as a c-Met agonist.

Example 5

Assay of c-Met Pathway Activation by IGTML4-4 Antibody in HUVEC

To compare agonisms of the IGTML4-4 antibody of Example 1, degrees of Akt or ERK phosphorylation as a critical index involved in down-stream signal transduction of c-Met and cell proliferation were measured using human umbilical vein endothelial cells (HUVECs, purchased from the American Type Culture Collection (ATCC, U.S.A.).

HUVECs were cultured in a 100-mm culture dish with an EGM-2 Bulletkit (Cat. No. CC-3162, available from Lonza) culture fluid. After being grown to about 80% of the culture dish, the HUVECs were reacted with a solution of 5 µg/ml of the IGTML4-4 antibody in a serum-free EBM culture liquid (Cat. No. CC-3121, available from Lonza) for about 30 minutes, and then a cell extract from the reaction product was analyzed by western blotting as follows.

In western blotting, 20 µg of the cell extract was separated using a Novex NuPAGE Bis-Tris Electrophoresis System (available from Invitrogen), and then was transferred onto a nitrocellulose membrane (Cat. No. LC2006, available from Invitrogen). After blocking with about 3% skim milk, the nitrocellulose membrane was incubated with a 1:1000 dilution of phospho-Akt (S473) antibody (Cat. No. 9271 L, available from Cell Signaling), Akt antibody (Cat. No. 9272S, available from Cell Signaling), phospho-Erk(p44/42 T202/Y204) antibody (Cat. No. 9106L, available from Cell Signaling), or Erk(p44/42) antibody (Cat. No. 9107S, available from Cell Signaling) at about 4° C. for about 18 hours. After sufficiently washing off unbound antibodies with a TBS-T solution, the remaining antibodies were reacted with a goat anti-rabbit IgG-HRP or goat anti-mouse IgG-HRP, depending on the type of the antibody, at room temperature for about 1 hour. After further sufficient washing with a TBS-T solution, a peroxidase substrate solution (Cat. No. 32106, available from Thermo Scientific Pierce ECL Western Blotting Substrate) was added to the reaction product to measure luminescence for comparison of expression levels.

Figure 3:
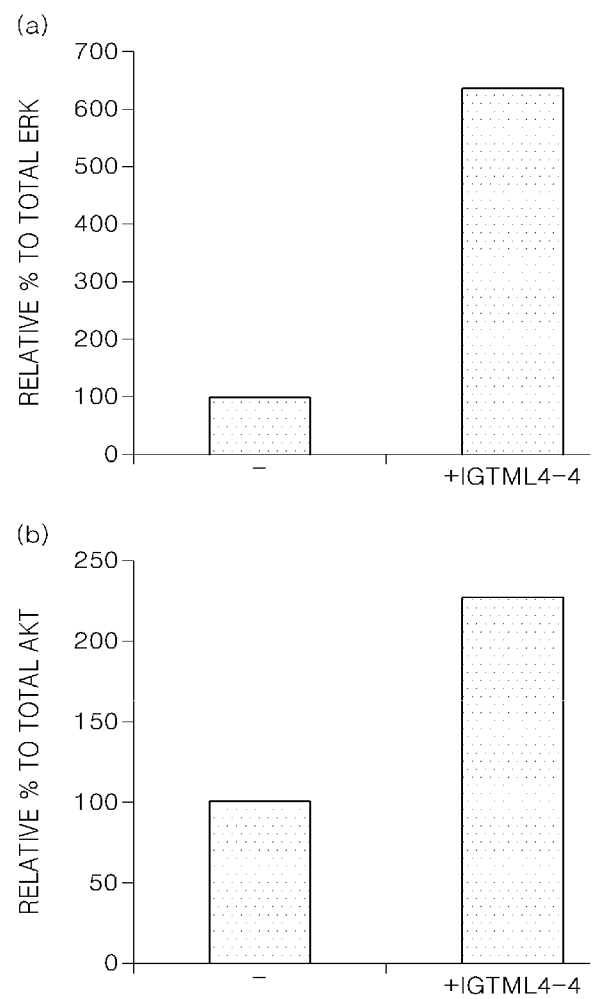
FIG. 3 is a graph presenting of Akt and ERK phosphorylation by an anti c-Met antibody according to an embodiment of the present disclosure.

As a result, the treatment with the IGTML4-4 antibody led to increases in degrees of Akt and ERK phosphorylation, as shown in FIG. 3. With or without the treatment with the IGTML4-4 antibody, no difference in the amounts of Akt and ERK was found. However, the degrees of Akt and ERK phosphorylation were significantly higher in the cells treated with the IGTML4-4 antibody.

Example 6

Assay of Primary Hepatocyte Proliferation by IGTML4-4 Antibody

Binding of c-Met and a hepatocyte growth factor (HGF) is known to facilitate growth of some cells. Such facilitated cell growth may be conducive to cell migration and wound healing. Thus, with the expectation that the IGTML4-4 antibody functioning as a c-Met agonist would facilitate growth of some cells, whether or not the treatment with the IGTML4-4 antibody facilitated proliferation of human primary hepatocytes was tested using an in vitro cell proliferation assay.

$3 \times 10^4$ primary hepatocytes (Cat. No. F00995, available from Celsis) and 100 µl of an InVitroGRO CP medium (Cat. No. Z99029, available from Celsis) were portioned to each well of a 96-well plate (well white plate, Cat. No. 3610, available from Corning), and were then incubated for about 24 hours. Afterward, 50 µl of a InVitroGRO HI medium (Incubation) (Cat. No. Z99009, available from Celsis) was added to a non-IGTML4-4 antibody treatment group, while dilutions of the IGTML4-4 antibody to concentrations of 2 µg/ml, 0.4 µg/ml, 0.08 µg/ml, or 0.016 µg/ml with an InVitroGRO HI medium (Incubation) (Cat. No. Z99009, Celsis) were added by 50 µl to IGTML4-4 antibody treatment groups, respectively. After incubation for about 72 hours, the numbers of cells were quantified using a CellTiter-Glo luminescent cell viability assay kit (Cat. No. G7570, available from Promega) and a luminometer (2104 multilabel reader, available from PerkinElmer). Primary hepatocytes treated with mouse IgG were used as a negative control group, and primary hepatocytes treated with HGF were used as a positive control group.

Figure 4:
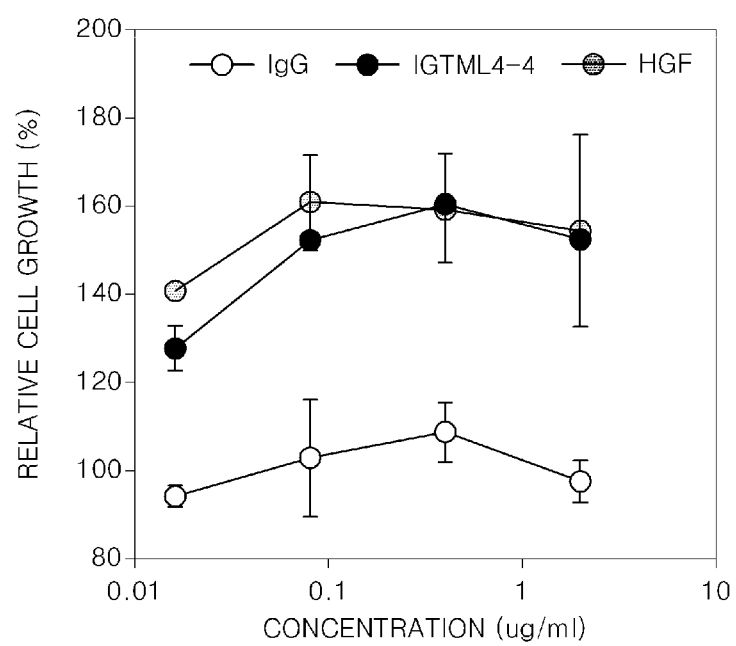
FIG. 4 presents results of counts of primary hepatocytes in anti c-Met antibody treatment groups according to an embodiment of the present disclosure.

Referring to FIG. 4, the IGTML4-4 treatment groups are found to include about 60% more primary hepatocytes as compared with the negative control groups treated with the mouse IgG. The numbers of primary hepatocytes in the IGTML4-4 treatment groups were similar to those in the positive control groups treated with HGF functioning as a c-Met ligand, indicating that, like HGF, the IGTML4-4 antibody is able to facilitate activation of c-Met, and thus proliferation of primary hepatocytes.

Example 7

Confirmation of Wound Healing Effect of IGTML4-4 Antibody on HUVEC

To investigate wound healing effects of c-Met activation due to the IGTML4-4 antibody, a wound healing assay was performed using HUVECs.

The wound healing assay is a method of measuring cell migration, in which scratches are made on confluent cell monolayers using a pipette tip, and disappearance of those scratches over time is observed.

A mixture of HUVECs with an EGM culture fluid was portioned into a 6-well plate, which was left until the HUVECs grew to cover about 95% of the area of the 6-well plate, and the culture fluid was removed therefrom. After being washed with a phosphate-buffered solution (PBS) once, the remaining HUVECs were scratched using a pipette tip. Mixtures of IGTML4-4 antibody with an EBM culture fluid (Lonza, Cat. No. CC-3121) containing a 0.1% fetal bovine serum (FBS) to concentrations of 0 µg/ml, 2.5 µg/ml, 5 µg/ml, and 10 µg/ml were portioned into each well. Wound conditions in the plate wells were microscopically observed immediately after the scratching and after incubation for about 12 hours, and differences of the images from the two observations were analyzed using image analyzer software (Wimscratch Quantitative Wound Healing Image Analysis).

Figure 5:
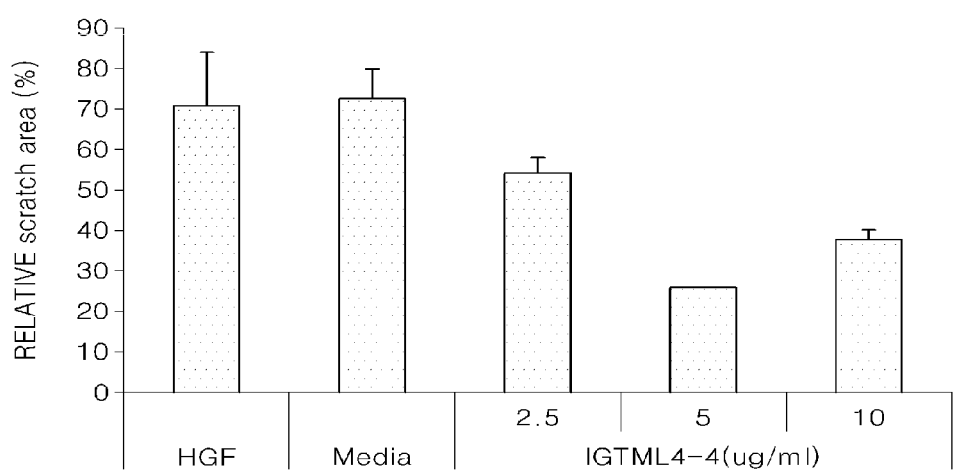
FIG. 5 is a graph presenting cell migration observation of human umbilical vein endothelial cells (HUVECs) in anti c-Met antibody treatment groups according to an embodiment of the present disclosure.

Referring to FIG. 5, with the treatment with the IGTML4-4 antibody, migration of HUVECs was significantly increased. The higher the IGTML4-4 antibody concentration, the greater the migration of the HUVECs was, with saturated migration of HUVECs at antibody concentrations of 10 µg/ml or higher.

Example 8

Confirmation of Increased Migration of HUVECs by IGTML4-4 Antibody

To determine whether cell migration increased due to the IGTML4-antibody, a cell migration assay was conducted using an xCelligence system (available from Roche), which counts the number of cells by measuring impedance varying with immobilization of a cell on a gold microelectrode array. In the cell migration array, a CIM-plate 16 (available from Roche) with separate upper and lower chambers, like a Boyden chamber, was used, wherein cells to be assayed were placed in the upper chamber, while an EBM culture fluid (Cat. No. CC-3121, available from Lonza) containing 2% FBS as a chemoattractant was added into the lower chamber. The upper chamber had a structure that allows generation of impedance from only those cells that have migrated through 8-μm pores.

Figure 6:
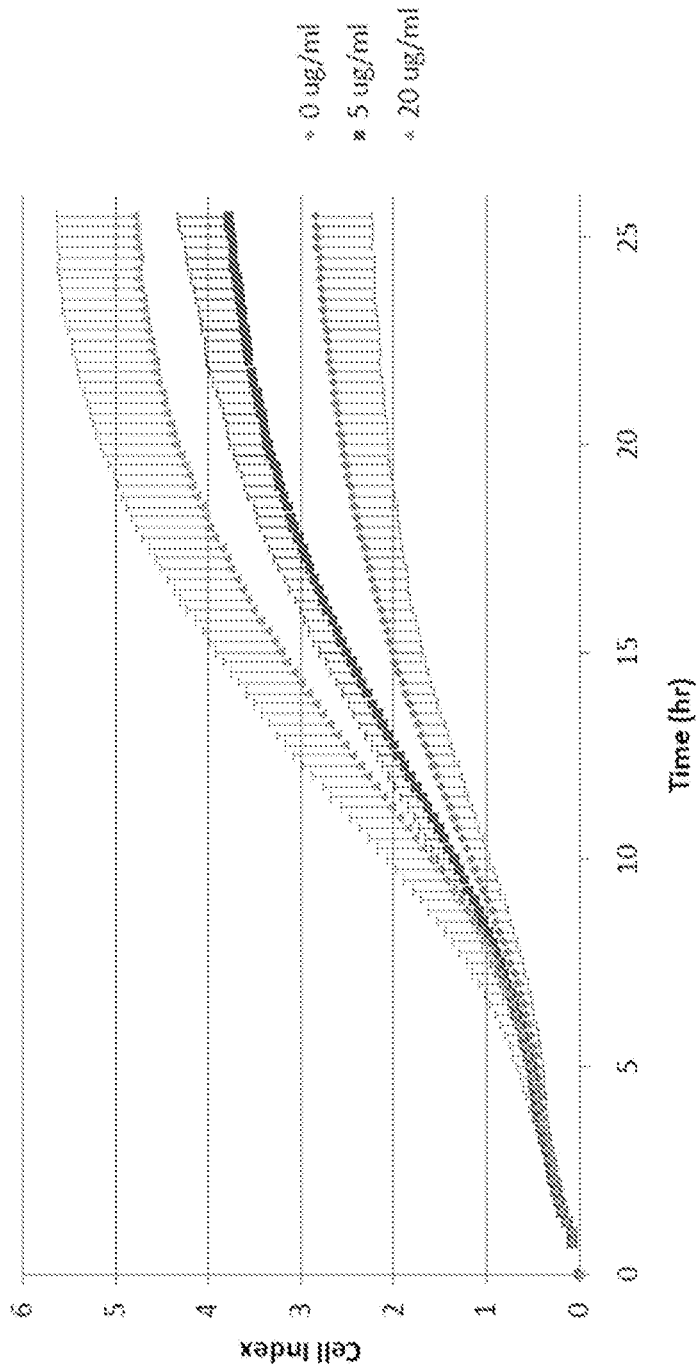
FIG. 6 is a graph of relative degrees of cell migration in anti c-Met antibody treatment groups having different antibody concentrations, according to an embodiment of the present disclosure.

In FIG. 6, 'Cell Index' means a relative impedance value. Referring to FIG. 6, the higher the IGTML4-4 antibody, the more the migration of cells was facilitated. In the treatment group with 20 μg/ml of the IGTML4-4 antibody, the cell migration was about 70% higher as compared with the control group not treated with the IGTML4-4 antibody.

Example 9

CDR Sequences of IGTML4-4 Antibody

Heavy-chain and light-chain CDR amino acid sequences of the IGTML4-4 antibody were identified, as shown in Table 1 above.

As described above, according to the one or more of the above embodiments of the present disclosure, use of the anti c-Met antibody, antigen-binding fragments thereof, or a pharmaceutical composition including the same may facilitate cell migration, and thus be effective in wound healing or tissue regeneration, and may efficiently facilitate cell proliferation.

It should be understood that the exemplary embodiments described herein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated anti c-Met antibody or antigen-binding fragment thereof comprising a heavy-chain variable region having heavy-chain complementarity determining region (CDR) amino acid sequences of SEQ ID NOs: 1, 2 and 3, and a light-chain variable region having light-chain CDR amino acid sequences of SEQ ID NOs: 4, 5, and 6.

2. The anti c-Met antibody or antigen-binding fragment of claim 1 comprising a heavy-chain variable region having an amino acid sequence of SEQ ID No. 7, and a light-chain variable region having an amino acid sequence of SEQ ID No. 8.

3. The anti c-Met antibody or antigen-binding fragment thereof of claim 1, wherein the c-Met is human c-Met, monkey c-Met, mouse c-Met, or rat c-Met.

4. The anti c-Met antibody or antigen-binding fragment thereof of claim 1, wherein the anti c-Met antibody is a monoclonal antibody.

5. An antigen-binding fragment of an anti c-Met antibody according to claim 1.

6. The antigen-binding fragment of claim 5, wherein the antigen-binding fragment is selected from the group consisting of scFv, (scFv)$_2$, Fab, Fab', and F(ab')$_2$.

7. A polynucleotide comprising a nucleotide sequence encoding the antibody or antigen-binding fragment of claim 1.

8. A polynucleotide comprising a nucleotide sequence encoding the antibody or antigen-binding fragment of claim 2.

9. A recombinant vector comprising the polynucleotide of claim 7.

10. A recombinant vector comprising the polynucleotide of claim 8.

11. A host cell comprising the polynucleotide of claim 9.

12. A host cell comprising the polynucleotide of claim 10.

13. A pharmaceutical composition comprising the antibody or antibody fragment of claim 1 and a pharmaceutically acceptable carrier, diluent, or excipient.

14. A pharmaceutical composition comprising the antibody or antibody fragment of claim 2 and a pharmaceutically acceptable carrier, diluent, or excipient.

15. A method for wound healing or tissue regeneration that comprises administering to a subject an anti c-Met antibody or antigen-binding fragment of claim 1.

16. The method of claim 15, wherein the method comprises administering an antigen-binding antibody fragment selected from the group consisting of scFv, (scFv)$_2$, Fab, Fab', and F(ab')$_2$.

17. A method for wound healing or tissue regeneration that comprises administering to a subject an anti c-Met antibody or antigen binding fragment thereof of claim 2.

18. The method of claim 17, wherein the method comprises administering an antigen-binding antibody fragment is selected from the group consisting of scFv, (scFv)$_2$, Fab, Fab', and F(ab')$_2$.

19. A method for facilitating cell proliferation that comprises administering to a subject the anti c-Met antibody or antigen-binding fragment thereof of claim 1.

20. The method of claim 19, wherein the method comprises administering an antigen-binding antibody fragment selected from the group consisting of scFv, (scFv)$_2$, Fab, Fab', and F(ab')$_2$.

21. A method for facilitating cell proliferation that comprises administering to a subject the anti c-Met antibody or antigen-binding fragment thereof of claim 2.

22. The method of claim 21, wherein the method comprises administering an antigen-binding antibody fragment selected from the group consisting of scFv, (scFv)$_2$, Fab, Fab', and F(ab')$_2$.

* * * * *